(12) United States Patent
Yerkes et al.

(10) Patent No.: US 10,172,355 B2
(45) Date of Patent: *Jan. 8, 2019

(54) SAFENED HERBICIDAL COMPOSITIONS INCLUDING 4-AMINO-3-CHLORO-5-FLUORO-6-(4-CHLORO-2-FLUORO-3-METHOXYPHENYL)PYRIDINE-2-CARBOXYLIC ACID OR A DERIVATIVE THEREOF FOR USE IN RICE

(71) Applicant: Dow AgroSciences LLC, Indianapolis, IN (US)

(72) Inventors: Carla N. Yerkes, Crawfordsville, IN (US); Richard K. Mann, Franklin, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/659,670

(22) Filed: Mar. 17, 2015

(65) Prior Publication Data
US 2015/0181872 A1 Jul. 2, 2015

Related U.S. Application Data

(63) Continuation of application No. 13/835,930, filed on Mar. 15, 2013, now abandoned.

(60) Provisional application No. 61/674,993, filed on Jul. 24, 2012.

(51) Int. Cl.
| | | |
|---|---|---|
| *A01N 43/40* | (2006.01) | |
| *A01N 43/54* | (2006.01) | |
| *A01N 43/653* | (2006.01) | |
| *A01N 47/40* | (2006.01) | |
| *A01N 47/30* | (2006.01) | |
| *A01N 47/34* | (2006.01) | |
| *A01N 43/58* | (2006.01) | |
| *A01N 43/34* | (2006.01) | |
| *A01N 41/10* | (2006.01) | |
| *A01N 25/32* | (2006.01) | |

(52) U.S. Cl.
CPC ............ *A01N 43/40* (2013.01); *A01N 25/32* (2013.01); *A01N 41/10* (2013.01); *A01N 43/34* (2013.01); *A01N 43/54* (2013.01); *A01N 43/58* (2013.01); *A01N 43/653* (2013.01); *A01N 47/30* (2013.01); *A01N 47/34* (2013.01); *A01N 47/40* (2013.01)

(58) Field of Classification Search
CPC ........ A01N 43/40; A01N 47/30; A01N 25/32; A01N 43/58; A01N 47/40; A01N 43/34; A01N 47/34; A01N 43/653; A01N 41/10; A01N 43/54
See application file for complete search history.

(56) References Cited

U.S. PATENT DOCUMENTS

| | | | | |
|---|---|---|---|---|
| 7,314,849 B2* | 1/2008 | Balko | ............... | A01N 43/40 504/244 |
| 8,791,048 B2* | 7/2014 | Yerkes | ............... | A01N 43/40 504/100 |
| 8,809,232 B2* | 8/2014 | Yerkes | ............... | A01N 43/40 504/100 |
| 8,841,233 B2* | 9/2014 | Yerkes | ............... | A01N 43/80 504/100 |
| 8,846,570 B2* | 9/2014 | Yerkes | ............... | A01N 43/40 504/100 |
| 8,871,680 B2* | 10/2014 | Yerkes | ............... | A01N 43/40 504/100 |
| 8,883,682 B2* | 11/2014 | Yerkes | ............... | A01N 43/40 504/129 |
| 8,883,688 B2* | 11/2014 | Yerkes | ............... | C07D 213/79 504/260 |

(Continued)

FOREIGN PATENT DOCUMENTS

| | | |
|---|---|---|
| WO | 2009/029518 A2 | 3/2009 |
| WO | PCT/US13/21018 | 12/2013 |

OTHER PUBLICATIONS

Tomlin, Clive. "Superseded Entries—Dicyclopentadiene." The Pesticide Manual. 15th ed. Farnham, Surrey, UK: British Crop Protection Council, 2009. 1223. Print.

*Primary Examiner* — John Pak
*Assistant Examiner* — Andriae M Holt

(57) ABSTRACT

A safened herbicidal composition for use in rice comprising a herbicidally effective amount of (a) a compound of formula (I):

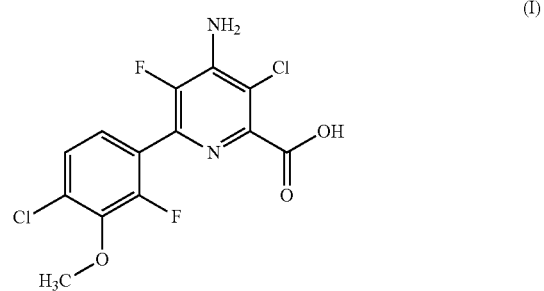

or an agriculturally acceptable salt or ester thereof and (b) a safener or a compatible herbicide capable of safening such as a chemical from the quinolinyloxyacetate family of chemicals, dicyclonon, daimuron, dimepiperate, fenclorim, furilazole, halosulfuron, isoxadifen-ethyl, mefenpyr-diethyl, naphthalic anhydride (NA), or agriculturally acceptable salts, esters, or mixtures thereof, for use in direct-seeded, water-seeded or transplanted rice.

24 Claims, No Drawings

(56) References Cited

U.S. PATENT DOCUMENTS

| | | | |
|---|---|---|---|
| 8,889,591 B2* | 11/2014 | Yerkes | A01N 43/40 504/100 |
| 8,895,470 B2* | 11/2014 | Yerkes | A01N 57/20 504/100 |
| 8,901,035 B2* | 12/2014 | Yerkes | A01N 43/40 504/100 |
| 8,906,825 B2* | 12/2014 | Mann | A01N 43/40 504/100 |
| 8,906,826 B2* | 12/2014 | Yerkes | A01N 43/40 504/100 |
| 8,962,523 B2 | 2/2015 | Rosinger et al. | |
| 9,169,217 B2* | 10/2015 | Yerkes | C07D 213/79 |
| 2010/0130361 A1* | 5/2010 | Yerkes | A01N 25/32 504/105 |
| 2010/0137137 A1 | 6/2010 | Rosinger et al. | |
| 2012/0115727 A1 | 5/2012 | Satchivi et al. | |

* cited by examiner

SAFENED HERBICIDAL COMPOSITIONS INCLUDING 4-AMINO-3-CHLORO-5-FLUORO-6-(4-CHLORO-2-FLUORO-3-METHOXYPHENYL)PYRIDINE-2-CARBOXYLIC ACID OR A DERIVATIVE THEREOF FOR USE IN RICE

This application is a Continuation of U.S. NonProvisional application Ser. No. 13/835,930 which was filed in the U.S. Patent and Trademark Office on Mar. 15, 2015 and claims the benefit of U.S. Provisional Application No. 61/674,993 which was filed in the U.S. Patent and Trademark Office on Jul. 24, 2012, the entire disclosure of which is hereby incorporated by reference in its entirety.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. Occasionally, however, such herbicides can injure the crop being protected in addition to the weeds and other vegetation intended to be controlled.

SUMMARY

Provided herein are safened herbicidal compositions for use in rice comprising a herbicidally effective amount of (a) a compound of the formula (I)

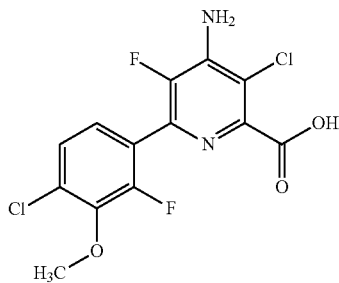

(I)

or an agriculturally acceptable salt or ester of thereof, and (b) a safener or a compatible herbicide capable of safening such as a chemical from the quinolinyloxyacetate family of chemicals, daimuron, dimepiperate, fenclorim, furilazole, halosulfuron, isoxadifen-ethyl, mefenpyr-diethyl, naphthalic anhydride (NA), or agriculturally acceptable salts, esters, or mixtures thereof. The compositions may also contain an agriculturally acceptable adjuvant or carrier.

Provided herein also are methods of controlling undesirable vegetation in rice comprising contacting the vegetation or applying to the soil or water to prevent the emergence or growth of vegetation a safened herbicidal composition comprising a herbicidally effective amount of (a) a compound of the formula (I)

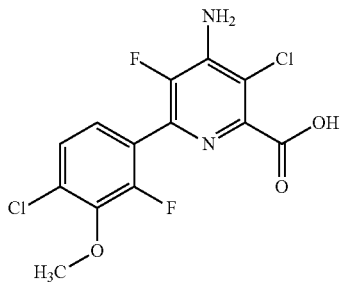

(I)

or an agriculturally acceptable salt or ester thereof and (b) a safener or a compatible herbicide capable of safening such as a chemical from the quinolinyloxyacetate family of chemicals, daimuron, dimepiperate, fenclorim, furilazole, halosulfuron, isoxadifen-ethyl, mefenpyr-diethyl, naphthalic anhydride (NA), or agriculturally acceptable salts, esters, or mixtures thereof.

DETAILED DESCRIPTION

Definitions

As used herein, the compound of formula (I) has the following structure:

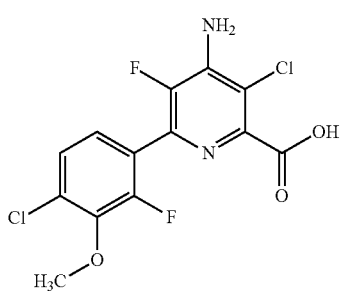

(I)

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

As used herein, safeners from the quinolinyloxyacetate family of chemicals are described in U.S. Pat. No. 4,902,340. Safeners from the quinolinyloxyacetate family of chemicals include derivatives of cloquintocet, such as cloquintocet acid, cloquintocet mexyl, cloquintocet triisopropylamine, and cloquintocet dimethylamine. Cloquintocet is the common name for [(5-chloro-8-quinolinyl)oxy]acetic acid. Cloquintocet's safening activity is described in The Pesticide Manual, Fourteenth Edition, 2006.

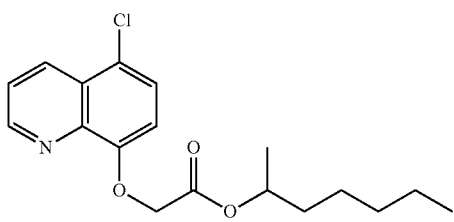 [SMILES: CCCCCC(C)OC(=O)COc1ccc(Cl)c2cccnc12]

As used herein, AD67 (MON 4660) is the common name for 4-(dichloroacetyl)-1-oxa-4-azaspiro-[4,5]decane. Its safening activity is described in The Pesticide Manual, Thirteenth Edition, 2003. AD67 (MON 4660) is known to be used as a safener in maize.

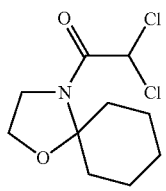 [SMILES: O=C(C(Cl)Cl)N1CCOC12CCCCC2]

As used herein, beflubutamid is the common name for 2-[14-fluoro-3-(trifluoromethyl)phenoxyl-N-(phenylmethyl)butanamide. Its herbicidal activity is described in The Pesticide Manual, Fourteenth Edition, 2006. Beflubutamid is a compound under development, used either alone or in mixtures with isoproturon, for pre- and early post-emergence control of broadleaf weeds, such as *Veronica persica*, *Lamium amplexicaule* and *Viola arvensis*, in wheat and barley.

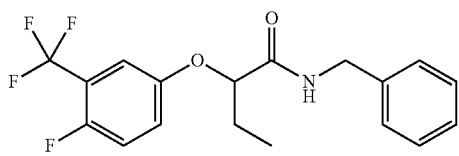 [SMILES: CCC(Oc1ccc(F)c(C(F)(F)F)c1)C(=O)NCc1ccccc1]

As used herein, bispyribac is the common name for 2,6-bis[(4,6-dimethoxy-2-pyrimidinyl)oxyl]-benzoic acid. Its herbicidal activity is described in The Pesticide Manual, Fourteenth Edition, 2006. Bispyribac-sodium controls grasses, sedges and broadleaf weeds in direct-seeded rice.

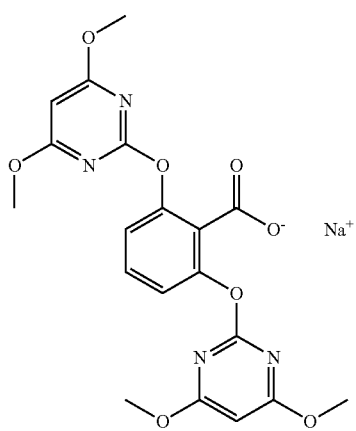 [SMILES: COc1cc(OC)nc(Oc2cccc(Oc3nc(OC)cc(OC)n3)c2C(=O)[O-])n1 ; [Na+]]

As used herein, carfentrazone is the common name for alpha-2-dichloro-5-[4-(difluoromethyl)-4,5-dihydro-3-methyl-5-oxo-1H-1,-2,4-triazol-1-yl]-4-fluorobenzenepropanoic acid. Its herbicidal activity is described in The Pesticide Manual, Fourteenth Edition, 2006. Carfentrazone-ethyl controls a wide range of broadleaf weeds in cereals and rice.

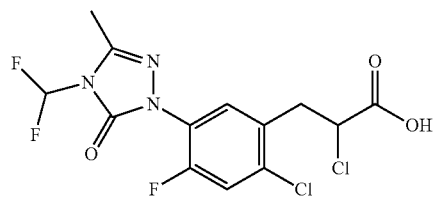 [SMILES: Cc1nn(-c2cc(CC(Cl)C(=O)O)c(Cl)cc2F)c(=O)n1C(F)F]

As used herein, cyhalofop is the common name for (2R)-2-[4-(4-cyano-2-fluorophenoxy)phenoxy]-propanoic acid. Its herbicidal activity is described in The Pesticide Manual, Fourteenth Edition, 2006. Cyhalofop-butyl is the preferred ester and controls grass weeds in rice.

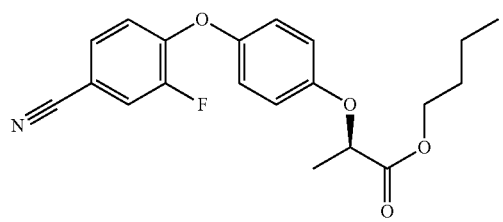 [SMILES: CCCCOC(=O)[C@@H](C)Oc1ccc(Oc2ccc(C#N)cc2F)cc1]

As used herein, daimuron is the common name for N-(4-methylphenyl)-N'-(1-methyl-1-phenylethyl)-urea. Its herbicidal activity is described in The Pesticide Manual, Fourteenth Edition, 2006. Daimuron controls cyperaceous and annual grass weeds in paddy rice.

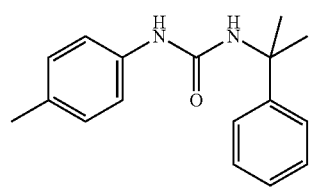 [SMILES: Cc1ccc(NC(=O)NC(C)(C)c2ccccc2)cc1]

As used herein, dichlormid is the common name for N,N-diallyl-2,2-dichloroacetamide. Its safening activity is described in The Pesticide Manual, Fourteenth Edition, 2006. Dichlormid is known to be used as a safener for maize and sorghum.

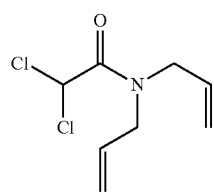

As used herein, dimepiperate is the common name for S-(1-methyl-1-phenylethyl)1-piperidine-carbothioate. Its herbicidal activity is described in The Pesticide Manual, Fourteenth Edition, 2006. Dimepiperate controls barnyardgrass (*Echinochloa crus-galli*) in paddy rice.

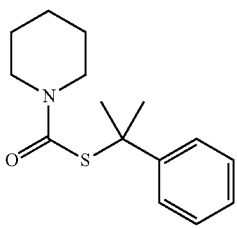 [SMILES: CC(C)(SC(=O)N1CCCCC1)c1ccccc1]

As used herein, fenclorim is the common name for 4,6-dichloro-2-phenylpyrimidine. Its safening activity is described in The Pesticide Manual, Fourteenth Edition, 2006. Fenclorim is known to be used as a safener in direct-seeded rice.

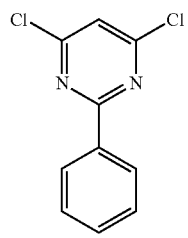 [SMILES: Clc1cc(Cl)nc(-c2ccccc2)n1]

As used herein, fluxofenim is the common name for 1-(4-chlorophenyl)-2,2,2-trifluoroethanone O-(1,3-dioxolan-2-ylmethyl)oxime. Its safening activity is described in The Pesticide Manual, Fourteenth Edition, 2006. Fluxofenim is known to be used as a safener in sorghum.

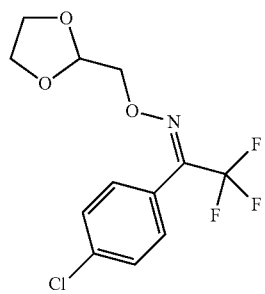 [SMILES: FC(F)(F)/C(=N/OCC1OCCO1)c1ccc(Cl)cc1]

As used herein, furilazole is the common name for 3-(dichloroacetyl)-5-(2-furanyl)-2,2-dimethyl-oxazolidine. Its safening activity is described in The Pesticide Manual, Fourteenth Edition, 2006. Furilazole is known to be used as a safener in maize.

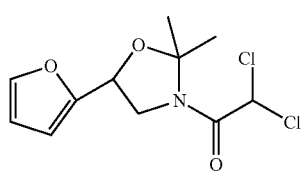 [SMILES: CC1(C)OC(c2ccco2)CN1C(=O)C(Cl)Cl]

As used herein, halosulfuron is the common name for 3-chloro-5-[[[[(4,6-dimethoxy-2-pyrimidinyl)-amino]carbonyl]amino]sulfony-1]-1-methyl-1H-pyrazole-4-carboxylic acid. Its herbicidal activity is described in The Pesticide Manual, Fourteenth Edition, 2006. Halosulfuron-methyl controls annual broadleaf weeds and nutsedge in rice.

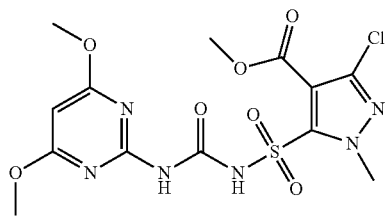 [SMILES: COC(=O)c1c(Cl)nn(C)c1S(=O)(=O)NC(=O)Nc1nc(OC)cc(OC)n1]

As used herein, isoxadifen-ethyl is the common name for ethyl 4,5-dihydro-5,5-diphenyl-3-isoxazole-carboxylate. Its safening activity is described in The Pesticide Manual, Fourteenth Edition, 2006. Isoxadifen-ethyl is known to be used as a safener in maize.

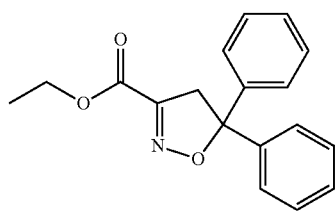 [SMILES: CCOC(=O)C1=NOC(c2ccccc2)(c2ccccc2)C1]

As used herein, mefenpyr-diethyl is the common name for 1-(2,4-dichlorophenyl)-4,5-dihydro-5-methyl-1H-pyrazole-3,5-dicarboxylic acid. Its safening activity is described in The Pesticide Manual, Fourteenth Edition, 2006. Mefenpyr-diethyl is known to be used as a safener in wheat, rye, triticale and barley.

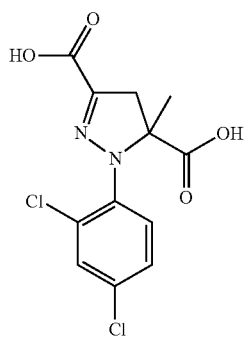 [SMILES: CC1(C(=O)O)CC(C(=O)O)=NN1c1ccc(Cl)cc1Cl]

As used herein, naphthalic anhydride (NA) is the common name for 1H,3H-naphtho[1,8-cd]pyran-1,3-dione. Its safening activity is described in Pesticide Outlook. *The Royal Society of Chemistry*. [Online] 2001. pp. 10-15. Naphthalic anhydride is known to be used as a safener in maize.

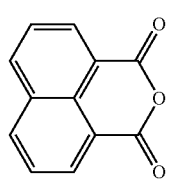 [SMILES: O=C1OC(=O)c2cccc3cccc1c23]

As used herein, norflurazon, is the common name for 4-chloro-5-(methylamino)-2-[3-(trifluoro-methyl)phenyl]-3(2H)-pyridazinon-e. Its herbicidal activity is described in The Pesticide Manual, Fourteenth Edition, 2006. Norflurazon is known to be used for the pre-emergence control of grasses and sedges, as well as some broadleaf weeds.

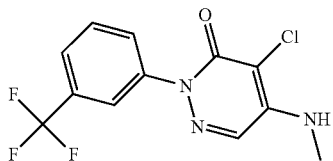 [SMILES: CNc1cnn(-c2cccc(C(F)(F)F)c2)c(=O)c1Cl]

As used herein, oxabetrinil is the common name for (.alpha.Z)-.alpha.-[(1,3-dioxolan-2-yflmethoxyimino]-benzeneacetonitrile. Its safening activity is described in The Pesticide Manual, Fourteenth Edition, 2006. Oxabetrinil is known to be used as a safener in sorghum.

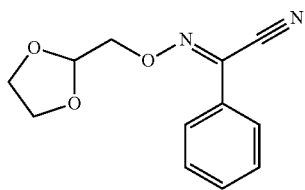 [SMILES: N#C/C(=N/OCC1OCCO1)c1ccccc1]

As used herein, pyriclor is the common name for 2,3,5-trichloro-4-pyridinol. Its activity is described in Buchholtz, K. P. Control of Quackgrass with Pyriclor. *Weed Science*. [Online]. 1968. pp. 439-441. Pyriclor is a herbicide for the control of quackgrass and *Echinochloa crusgalli* in direct-seeded rice.

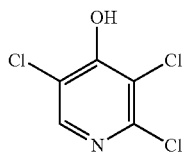

As used herein, sulcotrione is the common name for 2-[2-chloro-4-(methylsulfonyl)benzoyl]-1,3-cyclohexanedione. Its herbicidal activity is described in The Pesticide Manual, Fourteenth Edition, 2006. Sulcotrione controls grass and broadleaf weeds.

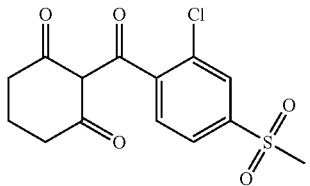 [SMILES: CS(=O)(=O)c1ccc(C(=O)C2C(=O)CCCC2=O)c(Cl)c1]

As used herein, herbicide means an active ingredient that kills, controls, or otherwise adversely modifies the growth of plants.

As used herein, a herbicidally effective or vegetation controlling amount is an amount of active ingredient which causes an adversely modifying effect and includes deviations from natural development, killing, regulation, desiccation, retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, as well as pre-emergence, post-emergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, and established vegetation.

As used herein, a safener is a compound that selectively protects crop plants from herbicide damage without significantly reducing activity in target weed species.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form. Exemplary salts include those derived from alkali or alkaline earth metals and those derived from ammonia and amines. Exemplary cations include sodium, potassium, magnesium, and aminium cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are safened herbicidal compositions for use in rice comprising a herbicidally effective amount of (a) a compound of the formula (I)

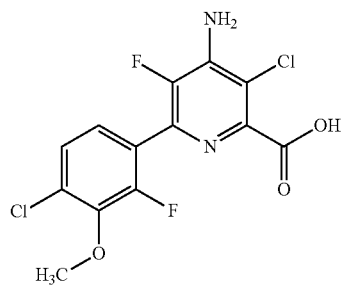

(I)

or an agriculturally acceptable salt or ester of thereof, and (b) a safener or a compatible herbicide capable of safening including, but not limited to, beflubutamid, bispyribac, carfentrazone, a chemical from the quinolinyloxyacetate family of chemicals, cyhalofop-butyl, daimuron, dichlormid, dimepiperate, fenclorim, fluxofenim, furilazole, halosulfuron, isoxadifen-ethyl, mefenpyr-diethyl, napthalic anhydride (NA), norflurazon, oxabetrinil, pyriclor, sulcotrione, AD67, or agriculturally acceptable salts, esters, or mixtures thereof.

Provided herein are also methods of controlling undesirable vegetation in rice comprising contacting the vegetation or applying to the soil or water adjacent thereto with a safened herbicidal composition including a herbicidally effective amount of (a) the compound of formula (I) or an agriculturally acceptable salt or ester thereof and (b) a safener or a compatible herbicide capable of safening including, but not limited to, beflubutamid, bispyribac, carfentrazone, a chemical from the quinolinyloxyacetate family of chemicals, cyhalofop-butyl, daimuron, dichlormid, dimepiperate, fenclorim, fluxofenim, furilazole, halosulfuron, isoxadifen-ethyl, mefenpyr-diethyl, norflurazon, oxabetrinil, pyriclor, sulcotrione, AD67, or agriculturally acceptable salts, esters, or mixtures thereof.

Rice plants to be protected from the adverse effect of undesirable plant growth may be damaged to a certain degree when an effective dose or overdose of herbicide is used. Safening means preventing the adverse effect of a herbicide on the rice plant, i.e., protecting the rice plant without, at the same time, noticeably influencing the herbicidal action on the undesirable plant growth, i.e., weeds, to be combated.

The compound of the formula (I) or an agriculturally acceptable salt or ester of thereof, and (b) a safener or a compatible herbicide capable of safening described herein can be applied either separately or together as part of a system. When part of a system, for example, the compound of the formula (I) or an agriculturally acceptable salt or ester of thereof, and (b) a safener or a compatible herbicide capable of safening described herein can be formulated in one composition, tank mixed, applied simultaneously, or applied sequentially.

Herbicidal activity is exhibited by the compounds of formula (I) when they are applied directly to a plant or to the area adjacent the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. The compositions of formula (I) described herein can be applied as a post-emergence application, or pre-emergence application, to relatively immature undesirable vegetation to achieve the maximum control of weeds.

The compositions and methods provided herein can be used to control weeds in rice crops, including, but not limited to, transplanted rice, water-seeded rice, and direct-seeded rice, and also in glyphosate-tolerant, 5-enolpyruvylshikimate-3-phosphate (EPSP) synthase inhibitor-tolerant, glufosinate-tolerant, glutamine synthetase inhibitor-tolerant, dicamba-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, phenoxy auxin-tolerant, pyridyloxy auxin-tolerant, auxin-tolerant, auxin transport inhibitor-tolerant, aryloxyphenoxypropionates-tolerant, acetyl CoA carboxylase (ACCase) inhibitor-tolerant, acetolactate synthase (ALS) or acetohydroxy acid synthase (AHAS) inhibitor-tolerant, 4-hydroxyphenyl-pyruvate dioxygenase (HPPD) inhibitor-tolerant, phytoene desaturase inhibitor-tolerant, carotenoid biosynthesis inhibitor-tolerant, protoporphyrinogen oxidase (PPO) inhibitor-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazines-tolerant, and bromoxynil-tolerant rice crops. The compositions and methods provided herein can be used with rice seeds, applied to nursery rice, direct-seeded rice, water-seeded rice and transplanted rice, as seed treatments, pre-plant treatments and post-emergence treatments.

The compositions and methods provided herein can be used to control undesirable vegetation consisting, for example, of grass, broadleaf and sedge weeds. For example, the combination of (a) compound (I) or agriculturally acceptable ester or salt thereof and (b) a safener or a compatible herbicide capable of safening including, but not limited to, beflubutamid, bispyribac, carfentrazone, a chemical from the quinolinyloxyacetate family of chemicals, cyhalofop, daimuron, dichlormid, dimepiperate, fenclorim, fluxofenim, furilazole, halosulfuron, isoxadifen-ethyl, mefenpyr-diethyl, naphthalic anhydride (NA), norflurazon, oxabetrinil, pyriclor, sulcotrione, AD67, or agriculturally acceptable salts, esters, or mixtures thereof is used to control undesirable vegetation including grass, broadleaf and sedge weeds. For example, the compositions and methods provided herein can be used to control undesirable vegetation including, but not limited to, undesirable vegetation of the weed genera *Echinochloa, Leptochloa, Brachiaria, Cyperus, Fimbristylis, Scirpus, Aeschynomene, Alternanthera, Alisma, Amaranthus, Ammannia, Eclipta, Heteranthera, Monochoria, Sagittaria, Sesbania,* and *Sphenoclea.* Examples of grass weeds controlled by the compositions and methods provided herein include, but are not limited to, *Brachiaria platyphylla* (Broadleaf signalgrass, BRAPP), *Echinochloa crus-galli* (Barnyardgrass, ECHCG), *Echinochloa colonum* (Junglerice, ECHCO), *Echinochloa oryzoides* (Early watergrass, ECHOR), *Leptochloa chinensis* (Chinese sprangletop, LEFCH), *Leptochloa fascicularis* (Bearded sprangletop, LEFFA), *Ischaemum rugosum Salisb.*

(Poaceae saramollagrass, ISCRU), and *Leptochloa panicoides* (Amazon sprangletop, LEFPA). Examples of sedge weeds controlled by the compositions and methods provided herein include, but are not limited to, *Cyperus difformis* (Smallflower flatsedge, CYPDI), *Cyperus esculentus* (Yellow nutsedge, CYPES), *Cyperus iria* (Rice flatsedge, CYPIR), *Cyperus rotundus* (Purple nutsedge, CYPRO), *Fimbristylis miliacea* (Globe fringerush, FIMMI), *Scirpus juncoides* (Smallflower flatsedge, SCPJU), and *Scirpus mucronatus* (Ricefield bulrush, SCPMU). Examples of broadleaf weeds controlled by the compositions and methods provided herein include, but are not limited to, *Aeschynomene species* (Jointvetch, AESSS), *Alternanthera philoxeroides* (Alligatorweed, ALRPH), *Alisma plantago-aquatica* (Common waterplantain, ALSPA), *Amaranthus* species (Pigweeds, AMASS), *Ammannia coccinea* (Purple ammannia, AMMCO), *Eclipta alba* (American false daisy, ECLAL), *Heteranthera limosa* (Ducksalad, HETLI), *Monochoria vaginalis* (Monochoria, MOOVA), *Sagittaria* species (Arrowhead, SAGMO), *Sesbania exaltata* (Hemp sesbania, SEBEX), and *Sphenoclea zeylanica* (Gooseweed, SPDZE). Additional examples of weeds controlled by the compositions and methods provided herein include, but are not limited to *Echinochloa oryzicola* (Vasinger) Vasinger (ECHPH, watergrass, late); *Lindernia dubia* (L.) Pennell (LIDDU, falsepimpernel, low); *Heteranthera reniformis* R. & P. (HETRE, mudplantain, roundleaf); *Murdannia nudiflora* (L.) Brenan (MUDNU, doveweed); *Alternanthera philoxeroides* (Mart.) Griseb. (ALRPH, alligatorweed); *Monochoria korsakowii* Regel & Maack (MOOKO; monochoria) and *Schoenoplectus maritimus* L. Lye (SCPMA, sea clubrush).

In the compounds and methods described herein, an agriculturally acceptable ester or salt of compound (I) is employed. An agriculturally acceptable ester, such as an aralkyl or alkyl ester, can be employed. The ester can be a $C_{1-4}$ alkyl ester, a n-butyl ester, a benzyl ester, or a substituted benzyl ester. Additionally, the carboxylic acid form of compound (I) or the carboxylate salt of the compound of formula (I) can be used.

In the compositions and methods described herein, the compound of formula (I) or salt or ester thereof is used in combination with a safener or a compatible herbicide capable of safening. The weight ratio of the compound of formula (I) or salt or ester thereof to the safener or a compatible herbicide capable of safening is within the range of from 2:1 to 1:32. The weight ratio of the compound of formula (I) or salt or ester thereof to the safener or a compatible herbicide capable of safening also can be within the range from 2:1 to 1:28, 2:1 to 1:24, 2:1 to 1:20, 2:1 to 1:18, 2:1 to 1:16, 2:1 to 1:14, 2:1 to 1:12, 2:1 to 1:10, 2:1 to 1:9, 2:1 to 1:8, 2:1 to 1:7, 2:1 to 1:6, 2:1 to 1:5, 2:1 to 1:4.5, 2:1 to 1:4, 2:1 to 1:3.5, 2:1 to 1:3, 2:1 to 1:2.5, 2:1 to 1:2, 2:1 to 1:1.5, 2:1 to 1:1, 1:1 to 1:32, 1:1 to 1:28, 1:1 to 1:24, 1:1 to 1:20, 1:1 to 1:18, 1:1 to 1:16, 1:1 to 1:14, 1:1 to 1:12, 1:1 to 1:10, 1:1 to 1:9, 1:1 to 1:8, 1:1 to 1:7, 1:1 to 1:6, 1:1 to 1:5, 1:1 to 1:4, 1:1 to 1:3.5, 1:1 to 1:3, 1:1 to 1:2.5, 1:1 to 1:2, or 1:1 to 1:1.5. Additionally, the weight ratio of the compound of formula (I) or salt or ester thereof to the safener or a compatible herbicide capable of safening can be 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:6, 1:7, 1:8, 1:9, 1:10, 1:11, 1:12, 1:13, 1:14, 1:15, 1:16, 1:18, 1:20, 1:24, 1:28, or 1:32.

The application rate will depend upon the particular type of weed to be controlled, the degree of control required, and the timing and method of application. In the compositions described herein the compound of formula (I) or salt or ester thereof can be applied at an application rate of from 1 grams acid equivalent per hectare (g ae/ha) to 300 g ae/ha based on the total amount of the compound of formula (I) or salt or ester thereof in the composition. Additionally, in the compositions described herein the compound of formula (I) or salt or ester thereof can be applied at an application rate of from 1 g ae/ha to 250 g ae/ha, 2 g ae/ha to 250 g ae/ha, 5 g ae/ha to 250 g ae/ha, 1 g ae/ha to 200 g ae/ha, 2 g ae/ha to 200 g ae/ha, 5 g ae/ha to 200 g ae/ha, 12.5 g ae/ha to 250 g ae/ha, 12.5 g ae/ha to 200 g ae/ha, 1 g ae/ha to 150 g ae/ha, 1 g ae/ha to 100 g ae/ha, 1 g ae/ha to 75 g ae/ha, 1 g ae/ha to 50 g ae/ha, 2 g ae/ha to 50 g ae/ha, or 5 g ae/ha to 50 g ae/ha based on the total amount of the compound of formula (I) or salt or ester thereof in the composition. In the compositions described herein the safener or a compatible herbicide capable of safening can be applied at an application rate of from 1 g ai/ha to 1200 g ai/ha. Additionally, in the compositions described herein the safener or a compatible herbicide capable of safening can be applied at an application rate of from 1 g ai/ha to 600 g ai/ha, 1 g ai/ha to 500 g ai/ha, 1 g ai/ha to 400 g ai/ha, 1 g ai/ha to 300 g ai/ha, 1 g ai/ha to 200 g ai/ha, 1 g ai/ha to 100 g ai/ha, 4 g ai/ha to 1200 g ai/ha, 4 g ai/ha to 600 g ai/ha, 50 g ai/ha to 600 g ai/ha, 50 g ai/ha to 500 g ai/ha, 50 g ai/ha to 400 g ai/ha, 50 g ai/ha to 300 g ai/ha, 50 g ai/ha to 200 g ai/ha, 50 g ai/ha to 150 g ai/ha, 50 g ai/ha to 100 g ai/ha, 100 g ai/ha to 1200 g ai/ha, 100 g ai/ha to 600 g ai/ha, 100 g ai/ha to 500 g ai/ha, 100 g ai/ha to 400 g ai/ha, 100 g ai/ha to 300 g ai/ha, or 100 g ai/ha to 200 g ai/ha based on the total amount of the safener or a compatible herbicide capable of safening in the composition. For example, the safener or a compatible herbicide capable of safening can be applied at a rate from 1 g ai/ha to 1200 g ai/ha and the compound of formula (I) of salt or ester thereof is applied at a rate from 1 g ae/ha to 300 g ae/ha.

The components of the mixtures described herein can be applied either separately or as part of a multipart herbicidal system.

The safened herbicide mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA; 4-CPB; 4-CPP; 2,4-D; 2,4-D choline salt, 2,4-D esters and amines, 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlomitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+ isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, fluroxypyr-meptyl, flurtamone, fluthiacet, fomesafen, foramsulfuron, fosamine, fumiclorac, furyloxyfen, glufosinate salts and esters, halauxifen, halauxifen-methyl, glufosinate-ammonium, glufosinate-P-ammonium, glyphosate salts and esters, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyrimnobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, SYN-523, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, triallate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The safened compositions and methods for their use described herein, can, further, be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes of action via single and/or multiple resistance mechanisms. The compound of formula (I) or salt or ester thereof and complementary herbicide or salt or ester thereof can be used in combination with herbicides that are selective for the crop being treated and which complement the spectrum of weeds controlled by these compounds at the application rate employed. The compositions described herein and other complementary herbicides can be applied at the same time, either as a combination formulation or as a tank mix.

The compositions and methods may be used in controlling undesirable vegetation in rice genetically modified to express specialized traits. Examples of specialized traits include agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The safened compositions described herein can also include with one or more additional herbicide safeners, such as AD-67 (MON 4660), benoxacor, benthiocarb, brassinolide, cyometrinil, dicyclonon, disulfoton, fenclorim, flurazole, fluxofenim, harpin proteins, jiecaowan, jiecaoxi, mephenate, oxabetrinil, R29148 and N-phenyl-sulfonylbenzoic acid amides, to enhance their selectivity.

The compositions and methods described herein can be used in combination with one or more seed treatments known to be employed in the safening of rice and compounds of formula (I), including naphthalic anhydride and CAS registry number 129531-12-0 (N-(2-Methoxybenzoyl)-4-[methylaminocarbonyl)amino]benzenesulfonamide) as depicted by:

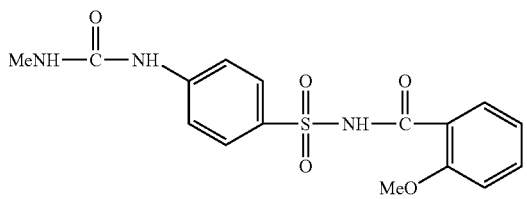

and CAS registry number 98967-94-3 (2-Thiophenecarboxylic acid, 3-[[(5,7-dimethyl[1,2,4]triazolo[1,5-a]pyrimidin-2-yl)sulfonyl]amino]-, methyl ester) as depicted by:

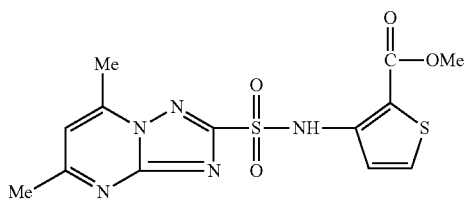 [SMILES: COC(=O)c1sccc1NS(=O)(=O)c1nc2nc(C)cc(C)n2n1]

In some embodiments, the safener is cloquintocet or an ester or salt thereof. In certain embodiments, cloquintocet is utilized to antagonize harmful effects of the compositions on rice. In some embodiments, the safener is cloquintocet (mexyl).

In some embodiments, the safener is isoxadifen-ethyl or an ester or salt thereof. In certain embodiments, isoxadifen-ethyl is utilized to antagonize harmful effects of the compositions on rice.

In some embodiments, the safener is furilazole. In some embodiments, the safener is furilazole or an ester or salt thereof. In certain embodiments, furilazole is utilized to antagonize harmful effects of the compositions on rice.

In some embodiments, the safener is mefenpyr-diethyl. In some embodiments, the safener is mefenpyr-diethyl or an ester or salt thereof. In certain embodiments, mefenpyr-diethyl is utilized to antagonize harmful effects of the compositions on rice.

The compositions described herein can be employed in combination with one or more plant growth regulators, such as 2,3,5-tri-iodobenzoic acid, IAA, IBA, naphthaleneacetamide, a-naphthaleneacetic acids, benzyladenine, 4-hydroxyphenethyl alcohol, kinetin, zeatin, endothal, pentachlorophenol, thidiazuron, tribufos, aviglycine, ethephon, maleic hydrazide, gibberellins, gibberellic acid, abscisic acid, ancymidol, fosamine, glyphosine, isopyrimol, jasmonic acid, maleic hydrazide, mepiquat, 2,3,5-tri-iodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol, and trinexapac. The plant growth regulator can be mixed with the compound of formula (I), or mixed with the compound of formula (I) to cause a preferentially advantageous effect on plants.

The compositions provided herein can further include one or more agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. The adjuvants or carriers can be solids, such as, for example, dusts, granules, water-dispersible granules, or wettable powders, or liquids, such as, for example, emulsifiable concentrates, solutions, emulsions or suspensions. Additionally, the adjuvants or carriers can also be provided as a pre-mix or tank mixed.

Suitable agricultural adjuvants and carriers are well known to those of skill in the art and include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Examples of liquid carriers that can be used in the compositions and methods described herein include water and organic solvents. Examples of useful organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is useful as a carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

The compositions described herein may further include one or more surface-active agents. Such surface-active agents can be used in both solid and liquid compositions, and can be designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide additionproducts, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, e.g., methyl esters. These materials, such as vegetable or seed oils and their esters, can be used interchangeably as an agricultural adjuvant, as a liquid carrier or as a surface active agent.

Other additives useful in the compositions provided herein include, but are not limited to, compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of active ingredients in the compositions described herein is generally from 0.0005 to 98 percent by weight. Additionally, concentration is from 0.0006 to 90 percent by weight can be used. In compositions designed to be employed as concentrates, the active ingredients, can be present in a concentration from 0.1 to 98 weight percent, or from 0.5 to 90 weight percent. Such compositions can be diluted with an inert carrier, such as, for example, water, before application. The diluted compositions usually applied to vegetation or the soil or water adjacent thereto can contain from 0.0006 to 15.0 weight percent active ingredient or from 0.001 to 10.0 weight percent.

The present compositions can be applied to vegetation or the soil or water adjacent thereto by the use of conventional ground or aerial dusters, sprayers, and granule applicators, by addition to irrigation or paddy water, and by other conventional means known to those skilled in the art.

The following Examples are presented to illustrate various aspects of the compositions and methods described herein and should not be construed as limitations to the claims.

EXAMPLES

Example I: Evaluation of Postemergence Foliar-Applied Herbicides and Safeners in Direct-Seeded Rice Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a surface area of 84.6 square centimeters ($cm^2$). When required to ensure good germination and healthy plants, a fungicide treatment and/or other chemical or physical treatment was applied. The plants were grown for 8-22 days in a greenhouse with an approximate 14 hr photoperiod which was maintained at about 29° C. during the day and 26° C. during the night. Nutrients (Peters Excel 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the second or third true leaf stage.

Treatments consisted of the acid or esters of 4-amino-3-chloro-5-fluoro-6-(4-chloro-2-fluoro-3-methoxy-phenyl) pyridine-2-carboxylic acid (compound A) and various safener components alone and in combination. Forms of compound A were applied on an acid equivalent basis. Safener components were applied on an active ingredient or acid equivalent basis depending on the compound.

Forms of compound A (compound of formula I) tested include:

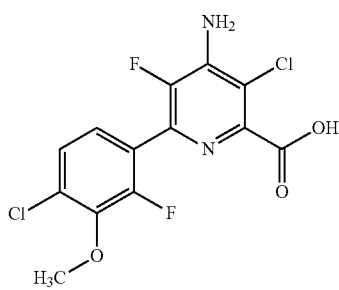

Compound A Acid

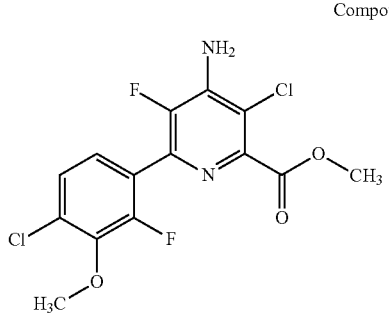

Compound A Methyl Ester

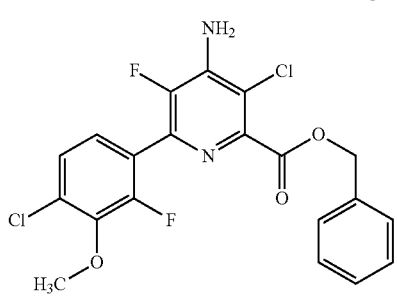

Compound A Benzyl Ester

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-dex crop oil concentrated to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) Agri-dex crop oil concentrate so that the final spray solutions contained 1.25% (v/v) Agri-dex crop oil concentrate.

For treatments comprised of technical compounds, weighed amounts were placed individually in 25 mL glass vials and dissolved in a volume of 97:3 v/v acetone/DMSO to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.5% (v/v) Agri-dex crop oil concentrate so that the final spray solutions contained 1.25% (v/v) Agri-dex crop oil concentrate. When technical materials were used, the concentrated stock solutions were added to the spray solutions so that the final acetone and DMSO concentrations of the application solutions were 16.2% and 0.5%, respectively.

For treatments comprised of formulated and technical compounds, weighed amounts of the technical materials were placed individually in 25 mL glass vials and dissolved in a volume of 97:3 v/v acetone/DMSO to obtain 12× stock solutions, and measured amounts of the formulated compounds were placed individually in 25 mL glass vials and diluted in a volume of 1.5% (v/v) Agri-dex crop oil concentrate or water to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of an appropriate amount of an aqueous mixture of 1.5% (v/v) Agri-dex crop oil concentrate so that the final spray solutions contained 1.25% (v/v) Agri-dex crop oil concentrate. When required, additional water and/or 97:3 v/v acetone/DMSO was added to individual application solutions so that the final acetone and DMSO concentrations of the application solutions being compared were 8.1% and 0.25%, respectively.

All stock solutions and applications solutions were visually inspected for compound compatibility prior to application. Spray solutions were applied to the plant material with an overhead Mandel track sprayer equipped with a 8002E nozzles calibrated to deliver 187 L/ha over an application area of 0.503 m² at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Some of the safener-herbicide combinations tested, application rates and ratios employed, plant species tested, and results are given in Tables 1-15. The results demonstrate the utility of Compound I acid and benzyl ester as post-emergence treatments in seeded rice, with increased tolerance of rice to Compound I benzyl ester in comparison to Compound I acid, and significant ECHCG weed control activity at rates safe to rice. In the Tables, DAA=Days After Application; ECHCG=*Echinochloa crus-galli*; NT=not tested; and ORYSA=*Orysa sativa*, Rice.

TABLE 1

Safening Activity in Rice (Cloquintocet-mexyl)

| | | | Visual Injury (%) - 21 DAA | | | | | |
|---|---|---|---|---|---|---|---|---|
| Compound A | Cloquintocet-mexyl | Herbicide to | ORYSA-'Neptune' | | ORYSA-'Wells' | | ORYSA-'Clearfield 171' | |
| g ae/ha | g ai/ha | safener ratio | Obs | Exp | Obs | Exp | Obs | Exp |
| Acid - 70 | 0 | — | 40 | — | 12 | — | 22 | — |
| Benzyl - 70 | 0 | | 5 | — | 0 | — | 0 | — |
| 0 | 70 | — | 0 | — | 0 | — | 0 | — |
| 0 | 140 | — | 0 | — | 0 | — | 0 | — |
| 0 | 280 | — | 0 | — | 0 | — | | — |
| Acid -70 | 70 | 1 to 1 | 17 | 40 | 3 | 12 | 8 | 22 |
| Acid - 70 | 140 | 1 to 2 | 17 | 40 | 0 | 12 | 3 | 22 |
| Acid - 70 | 280 | 1 to 4 | 10 | 40 | 0 | 12 | 3 | 22 |
| Benzyl -70 | 70 | 1 to 1 | 3 | 5 | 0 | 0 | 0 | 0 |
| Benzyl -70 | 140 | 1 to 2 | 3 | 5 | 0 | 0 | 0 | 0 |
| Benzyl -70 | 280 | 1 to 4 | 0 | 5 | 0 | 0 | 0 | 0 |

TABLE 2

Safening Activity in Rice (Daimuron)

| | | | Visual Injury (%) - 21 DAA | | | | | |
|---|---|---|---|---|---|---|---|---|
| Compound A | Daimuron | Herbicide to | ORYSA-'Neptune' | | ORYSA-'Wells' | | ORYSA-'Clearfield 171' | |
| g ae/ha | g ai/ha | safener ratio | Obs | Exp | Obs | Exp | Obs | Exp |
| Acid - 70 | 0 | — | 40 | — | 12 | — | 22 | — |
| Benzyl -70 | 0 | | 5 | — | 0 | — | 0 | — |
| 0 | 70 | — | 0 | — | 0 | — | 0 | — |
| 0 | 140 | — | 0 | — | 0 | — | 0 | — |
| 0 | 280 | — | 0 | — | 0 | — | | — |
| Acid - 70 | 70 | 1 to 1 | 35 | 40 | 3 | 12 | 17 | 22 |
| Acid - 70 | 140 | 1 to 2 | 37 | 40 | 3 | 12 | 15 | 22 |
| Acid - 70 | 280 | 1 to 4 | 22 | 40 | 7 | 12 | 20 | 22 |
| Benzyl - 70 | 70 | 1 to 1 | 8 | 5 | 3 | 0 | 0 | 0 |
| Benzyl - 70 | 140 | 1 to 2 | 20 | 5 | 0 | 0 | 0 | 0 |
| Benzyl - 70 | 280 | 1 to 4 | 15 | 5 | 0 | 0 | 0 | 0 |

TABLE 3

Safening Activity in Rice (Diclormid)

| | | | Visual Injury (%) - 20 DAA | | | |
|---|---|---|---|---|---|---|
| Compound A | Dichlormid | Herbicide to safener | ORYSA-'Clearfield 171' | | ECHCG | |
| g ae/ha | g ai/ha | ratio | Obs | Exp | Obs | Exp |
| Acid - 140 | 0 | — | 43 | — | 98 | — |
| Benzyl - 140 | 0 | — | 13 | — | 98 | — |
| 0 | 140 | — | 0 | — | NT | — |
| 0 | 280 | — | 0 | — | 0 | — |
| Acid - 140 | 140 | 1 to 1 | 63 | 43 | 99 | NT |
| Acid - 140 | 280 | 1 to 2 | 55 | 43 | 99 | 98 |
| Benzyl - 140 | 140 | 1 to 1 | 12 | 13 | 99 | NT |
| Benzyl - 140 | 280 | 1 to 2 | 8 | 13 | 98 | 98 |

TABLE 4

Safening Activity in Rice (Dimepiperate)

| | | | Visual Injury (%) - 20 DAA | | | |
|---|---|---|---|---|---|---|
| Compound A | Dimepiperate | Herbicide to safener | ORYSA-'Clearfield 171' | | ECHCG | |
| g ae/ha | g ai/ha | ratio | Obs | Exp | Obs | Exp |
| Acid - 140 | 0 | — | 43 | — | 98 | — |
| Benzyl - 140 | 0 | | 13 | — | 98 | — |
| 0 | 140 | — | 7 | — | 0 | — |
| 0 | 280 | — | 3 | — | 0 | — |
| Acid - 140 | 140 | 1 to 1 | 60 | 47 | 98 | 98 |
| Acid - 140 | 280 | 1 to 2 | 65 | 45 | 99 | 98 |
| Benzyl - 140 | 140 | 1 to 1 | 7 | 19 | 96 | 98 |
| Benzyl - 140 | 280 | 1 to 2 | 20 | 16 | 97 | 98 |

TABLE 5

Safening Activity in Rice (Furilazole)

| | | | Visual Injury (%) - 20 DAA | | | |
|---|---|---|---|---|---|---|
| Compound A | Furilazole | Herbicide to safener | ORYSA-'Clearfield 171' | | ECHCG | |
| g ae/ha | g ai/ha | ratio | Obs | Exp | Obs | Exp |
| Acid - 140 | 0 | — | 38 | — | 96 | — |
| Methyl - 140 | 0 | | 12 | — | 98 | — |
| Benzyl - 140 | 0 | | 15 | — | 99 | — |
| 0 | 140 | — | 0 | — | 0 | — |
| 0 | 280 | | 0 | — | 0 | — |
| Acid - 140 | 140 | 1 to 1 | 30 | 38 | 99 | 96 |
| Acid - 140 | 280 | 1 to 2 | 20 | 38 | 99 | 96 |
| Methyl - 140 | 140 | 1 to 1 | 0 | 12 | 93 | 98 |
| Methyl - 140 | 280 | 1 to 2 | 0 | 12 | 95 | 98 |
| Benzyl - 140 | 140 | 1 to 1 | 17 | 15 | 99 | 99 |
| Benzyl - 140 | 280 | 1 to 2 | 20 | 15 | 100 | 99 |

TABLE 6

Safening Activity in Rice (Furilazole)

| | | | Visual Injury (%) - 20 DAA | | | |
|---|---|---|---|---|---|---|
| Compound A | Furilazole | Herbicide to safener | ORYSA-'Clearfield 171' | | ECHCG | |
| g ae/ha | g ai/ha | ratio | Obs | Exp | Obs | Exp |
| Acid - 140 | 0 | — | 43 | — | 98 | — |
| Benzyl - 140 | 0 | | 13 | — | 98 | — |
| 0 | 140 | | 7 | — | 0 | — |
| 0 | 280 | — | 18 | — | 0 | — |
| Acid - 140 | 140 | 1 to 1 | 57 | 47 | 96 | 98 |
| Acid - 140 | 280 | 1 to 2 | 55 | 54 | 95 | 98 |
| Benzyl - 140 | 140 | 1 to 1 | 12 | 19 | 96 | 98 |
| Benzyl - 140 | 280 | 1 to 2 | 8 | 29 | 95 | 98 |

TABLE 7

Safening Activity in Rice (Isoxadifen-ethyl)

| | | | Visual Injury (%) - 21 DAA | | | | | |
|---|---|---|---|---|---|---|---|---|
| Compound A | Isoxadifen-ethyl | Herbicide to safener ratio | ORYSA-'Neptune' | | ORYSA-'Wells' | | ORYSA-'Clearfield 171' | |
| g ae/ha | g ai/ha | | Obs | Exp | Obs | Exp | Obs | Exp |
| Acid - 70 | 0 | — | 40 | — | 12 | — | 22 | — |
| Benzyl - 70 | 0 | | 5 | — | 0 | — | 0 | — |
| 0 | 70 | | 0 | — | 0 | — | 0 | — |
| 0 | 140 | — | 0 | — | 0 | — | 0 | — |
| 0 | 280 | | 0 | — | 0 | — | | — |
| Acid - 70 | 70 | 1 to 1 | 0 | 40 | 0 | 12 | 0 | 22 |
| Acid - 70 | 140 | 1 to 2 | 0 | 40 | 0 | 12 | 0 | 22 |
| Acid - 70 | 280 | 1 to 4 | 0 | 40 | 3 | 12 | 0 | 22 |
| Benzyl - 70 | 70 | 1 to 1 | 0 | 5 | 0 | 0 | 0 | 0 |
| Benzyl - 70 | 140 | 1 to 2 | 0 | 5 | 0 | 0 | 0 | 0 |
| Benzyl - 70 | 280 | 1 to 4 | 0 | 5 | 0 | 0 | 0 | 0 |

TABLE 8

Safening Activity in Rice (Mefenpyr-diethyl)

| | | | Visual Injury (%) - 21 DAA | | | | | |
|---|---|---|---|---|---|---|---|---|
| Compound A | Mefenpyr-diethyl | Herbicide to safener ratio | ORYSA-'Neptune' | | ORYSA-'Wells' | | ORYSA-'Clearfied 171' | |
| g ae/ha | g ai/ha | | Obs | Exp | Obs | Exp | Obs | Exp |
| Acid - 70 | 0 | — | 40 | — | 12 | — | 22 | — |
| Benzyl - 70 | 0 | | 5 | — | 0 | — | 0 | — |
| 0 | 70 | | 0 | — | 0 | — | 3 | — |
| 0 | 140 | — | 0 | — | 0 | — | 0 | — |
| 0 | 280 | | 3 | — | 0 | — | | — |
| Acid - 70 | 70 | 1 to 1 | 37 | 40 | 7 | 12 | 22 | 24 |
| Acid - 70 | 140 | 1 to 2 | 33 | 40 | 12 | 12 | 15 | 22 |
| Acid - 70 | 280 | 1 to 4 | 25 | 42 | 10 | 12 | 18 | 22 |
| Benzyl - 70 | 70 | 1 to 1 | 23 | 5 | 12 | 0 | 12 | 3 |
| Benzyl - 70 | 140 | 1 to 2 | 25 | 5 | 10 | 0 | 7 | 0 |
| Benzyl - 70 | 280 | 1 to 4 | 18 | 8 | 3 | 0 | 7 | 0 |

TABLE 9

Safening Activity in Rice (Naphthalic anhydride)

| Compound A | Naphthalic anhydride | Herbicide to safener | ORYSA-'Clearfield 171' | | ECHCG | |
|---|---|---|---|---|---|---|
| | | | Visual Injury (%) - 20 DAA | | | |
| g ae/ha | g ai/ha | ratio | Obs | Exp | Obs | Exp |
| Acid - 140 | 0 | — | 38 | — | 96 | — |
| Methyl - 140 | 0 | — | 12 | — | 98 | — |
| Benzyl - 140 | 0 | — | 15 | — | 99 | — |
| 0 | 140 | — | 0 | — | 0 | — |
| 0 | 280 | — | 3 | — | 0 | — |
| Acid - 140 | 140 | 1 to 1 | 38 | 38 | 98 | 96 |
| Acid - 140 | 280 | 1 to 2 | 20 | 40 | 99 | 96 |
| Methyl - 140 | 140 | 1 to 1 | 8 | 12 | 98 | 98 |
| Methyl - 140 | 280 | 1 to 2 | 8 | 15 | 99 | 98 |
| Benzyl - 140 | 140 | 1 to 1 | 10 | 15 | 99 | 99 |
| Benzyl - 140 | 280 | 1 to 2 | 12 | 18 | 98 | 99 |

TABLE 10

Safening Activity in Rice (Naphthalic anhydride)

| Compound A | Naphthalic anhydride | Herbicide to safener | ORYSA-'Clearfield 171' | | ECHCG | |
|---|---|---|---|---|---|---|
| | | | Visual Injury (%) - 20 DAA | | | |
| g ae/ha | g ai/ha | ratio | Obs | Exp | Obs | Exp |
| Acid - 140 | 0 | — | 43 | — | 98 | — |
| Benzyl - 140 | 0 | — | 13 | — | 98 | — |
| 0 | 140 | — | 0 | — | 0 | — |
| 0 | 280 | — | 0 | — | 0 | — |
| Acid - 140 | 140 | 1 to 1 | 48 | 43 | 96 | 98 |
| Acid - 140 | 280 | 1 to 2 | 58 | 43 | 95 | 98 |
| Benzyl - 140 | 140 | 1 to 1 | 13 | 13 | 95 | 98 |
| Benzyl - 140 | 280 | 1 to 2 | 3 | 13 | 98 | 98 |

TABLE 11

Safening Activity in Rice (Dicyclonon)

| Compound A | Dicyclonon | Herbicide to safener | ORYSA-'Clearfield 171' | | ECHCG | |
|---|---|---|---|---|---|---|
| | | | Visual Injury (%) - 20 DAA | | | |
| g ae/ha | g ai/ha | ratio | Obs | Exp | Obs | Exp |
| Acid - 140 | 0 | — | 38 | — | 96 | — |
| Methyl - 140 | 0 | — | 12 | — | 98 | — |
| Benzyl - 140 | 0 | — | 15 | — | 99 | — |
| 0 | 140 | — | 0 | — | NT | — |
| 0 | 280 | — | 0 | — | 3 | — |
| Acid - 140 | 140 | 1 to 1 | 57 | 38 | 99 | NT |
| Acid - 140 | 280 | 1 to 2 | 38 | 38 | 99 | 96 |
| Methyl - 140 | 140 | 1 to 1 | 3 | 12 | 98 | NT |
| Methyl - 140 | 280 | 1 to 2 | 5 | 12 | 98 | 98 |
| Benzyl - 140 | 140 | 1 to 1 | 18 | 15 | 98 | NT |
| Benzyl - 140 | 280 | 1 to 2 | 17 | 15 | 98 | 99 |

TABLE 12

Safening Activity in Rice (Dicyclonon)

| Compound A | Dicyclonon | Herbicide to safener | ORYSA-'Clearfield 171' | | ECHCG | |
|---|---|---|---|---|---|---|
| | | | Visual Injury (%) - 20 DAA | | | |
| g ae/ha | g ai/ha | ratio | Obs | Exp | Obs | Exp |
| Acid - 140 | 0 | — | 43 | — | 98 | — |
| Benzyl - 140 | 0 | — | 13 | — | 98 | — |
| 0 | 140 | — | 0 | — | NT | — |
| 0 | 280 | — | 3 | — | 0 | — |
| Acid - 140 | 140 | 1 to 1 | 45 | 43 | 98 | NT |
| Acid - 140 | 280 | 1 to 2 | 57 | 45 | 99 | 98 |
| Benzyl - 140 | 140 | 1 to 1 | 5 | 13 | 98 | NT |
| Benzyl - 140 | 280 | 1 to 2 | 8 | 16 | 95 | 98 |

TABLE 13

Safening Activity in Rice (Fenclorim)

| Compound A | Fenclorim | Herbicide to safener | ORYSA-'Clearfield 171' | | ECHCG | |
|---|---|---|---|---|---|---|
| | | | Visual Injury (%) - 20 DAA | | | |
| g ae/ha | g ai/ha | ratio | Obs | Exp | Obs | Exp |
| Acid - 140 | 0 | — | 38 | — | 96 | — |
| Methyl - 140 | 0 | — | 12 | — | 98 | — |
| Benzyl - 140 | 0 | — | 15 | — | 99 | — |
| 0 | 140 | — | 0 | — | 0 | — |
| 0 | 280 | — | 0 | — | 0 | — |
| Acid - 140 | 140 | 1 to 1 | 22 | 38 | 98 | 96 |
| Acid - 140 | 280 | 1 to 2 | 20 | 38 | 99 | 96 |
| Methyl - 140 | 140 | 1 to 1 | 7 | 12 | 98 | 98 |
| Methyl - 140 | 280 | 1 to 2 | 0 | 12 | 95 | 98 |
| Benzyl - 140 | 140 | 1 to 1 | 10 | 15 | 99 | 99 |
| Benzyl - 140 | 280 | 1 to 2 | 5 | 15 | 99 | 99 |

TABLE 14

Safening Activity in Rice (Fenclorim)

| Compound A | Fenclorim | Herbicide to safener | ORYSA-'Clearfield 171' | | ECHCG | |
|---|---|---|---|---|---|---|
| | | | Visual Injury (%) - 20 DAA | | | |
| g ae/ha | g ai/ha | ratio | Obs | Exp | Obs | Exp |
| Acid - 140 | 0 | — | 43 | — | 98 | — |
| Benzyl - 140 | 0 | — | 13 | — | 98 | — |
| 0 | 140 | — | 0 | — | 0 | — |
| 0 | 280 | — | 0 | — | 0 | — |
| Acid - 140 | 140 | 1 to 1 | 58 | 43 | 98 | 98 |
| Acid - 140 | 280 | 1 to 2 | 32 | 43 | 98 | 98 |
| Benzyl - 140 | 140 | 1 to 1 | 3 | 13 | 95 | 98 |
| Benzyl - 140 | 280 | 1 to 2 | 0 | 13 | 98 | 98 |

TABLE 15

Post-emergence Foliar Activity of Compound A

| Compound A g ae/ha | ORYSA 'Clearfield 171' | ORYSA 'Wells' | ECHCG |
|---|---|---|---|
| | Mean Visual Injury (%) - 20-22 DAA | | |
| Acid - 32 | 24 | 12 | 96 |
| Acid - 16 | 11 | 7 | 95 |
| Acid - 8 | 2 | 0 | 91 |

TABLE 15-continued

Post-emergence Foliar Activity of Compound A

| Compound A g ae/ha | Mean Visual Injury (%) - 20-22 DAA | | |
|---|---|---|---|
| | ORYSA 'Clearfield 171' | ORYSA 'Wells' | ECHCG |
| Acid - 4 | 0 | 0 | 81 |
| Acid - 2 | 0 | 0 | 57 |
| Benzyl - 32 | 3 | 3 | 96 |
| Benzyl - 16 | 8 | 3 | 95 |
| Benzyl - 8 | 0 | 0 | 94 |
| Benzyl - 4 | 0 | 0 | 91 |
| Benzyl - 2 | 0 | 0 | 63 |
| 0 | 0 | 0 | 0 |

Example II: Evaluation of In-Water Applied Herbicides and Safeners in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters ($cm^2$) leaving a headspace of 3 centimeters (cm) in each pot. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 860 mL of mud contained in 32-oz. non-perforated plastic pots with a surface area of 86.59 $cm^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 h photoperiod which was maintained at about 29'C during the day and about 26° C. during the night. Nutrients were added as Osmocote® (17:6:10, N:P:K+minor nutrients) at 2 g per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the second or third true leaf stage.

Treatments consisted of the acid or esters of 4-amino-3-chloro-5-fluoro-6-(4-chloro-2-fluoro-3-methoxy-phenyl)pyridine-2-carboxylic acid (compound A) and various safeners alone and in combination. Forms of compound A were applied on an acid equivalent basis. Safener components were applied on an active ingredient or acid equivalent basis depending on the compound.

Forms of compound A (compound of formula I) tested include:

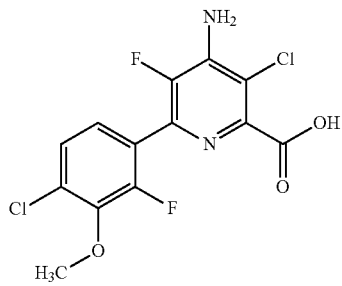

Compound A Acid

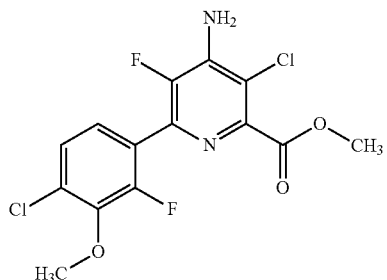

Compound A Methyl Ester

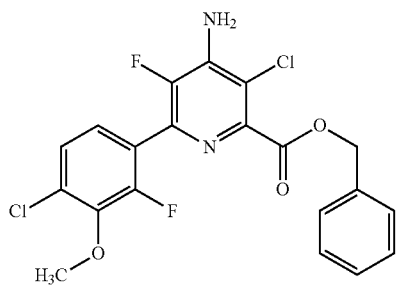

Compound A Benzyl Ester

Treatment requirements for each compound or herbicidal component were calculated based upon the rates being tested, the concentration of active ingredient or acid equivalent in the formulation, an application volume of 2 mL per component per pot, and an application area of 86.59 $cm^2$ per pot.

For formulated compounds, a measured amount was placed in an individual 100 or 200 mL glass vial and was dissolved in a volume of 1.25% (v/v) Agri-Dex® crop oil concentrate to obtain application solutions. If the test compound did not dissolve readily, the mixture was warmed and/or sonicated.

For technical grade compounds, a weighed amount can be placed in an individual 100 to 200 mL glass vial and dissolved in a volume of acetone to obtain concentrated stock solutions. If the test compound does not dissolve readily, the mixture can be warmed and/or sonicated. The concentrated stock solutions obtained can be diluted with an equivalent volume of an aqueous mixture containing 2.5% (v/v) crop oil concentrate so that the final application solutions contain 1.25% (v/v) crop oil concentrate.

Applications were made by injecting with a pipetter appropriate amounts of the application solutions, individually and sequentially, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

Some of the safener-herbicide combinations tested, application rates and ratios employed, plant species tested, and results are given in Tables 16-17. The results demonstrate the utility of Compound A acid and benzyl ester as in-water treatments in water-seeded rice and flooded transplanted rice, with significant ECHCG weed control activity at rates safe to rice. Based on the relative rice and barnyardgrass responses to Compound A acid and Compound A benzyl ester, Compound A benzyl ester showed an improved selectivity margin over that of the acid. In the Tables, DAA=Days After Application; ECHCG=*Echinochloa crus-galli*; NT=not tested; and ORYSA=*Orysa sativa*, Rice.

TABLE 16

Safening Activity in Rice (Fenclorim)

| Compound A | Isoxadifen-ethyl | Herbicide to safener | Visual Injury (%) - 21 DAA ORYSA - 'M202' | |
|---|---|---|---|---|
| g ae/ha | g ai/ha | ratio | Obs | Exp |
| Methyl - 140 | 0 | | 17.5 | — |
| 0 | 140 | | 0 | — |
| 0 | 280 | — | 0 | — |
| 0 | 560 | | 0 | — |
| Methyl - 140 | 140 | 1 to 1 | 0 | 17.5 |
| Methyl - 140 | 280 | 1 to 2 | 0 | 17.5 |
| Methyl - 140 | 560 | 1 to 4 | 0 | 17.5 |

TABLE 17

In-Water Applied Activity of Compound A

| | Mean Visual Injury (%) - 21 DAA | | |
|---|---|---|---|
| Compound A* g ae/ha | ORYSA - 'M202' | ORYSA - 'Wells' | ECHCG |
| Acid - 140 | 25 | 8 | 95 |
| Acid - 70 | 3 | 0 | 63 |
| Acid - 35 | 0 | 0 | 10 |
| Acid - 17.5 | 0 | 0 | 0 |
| Acid - 8.75 | 0 | 0 | 0 |
| Benzyl - 140 | 22 | 15 | 100 |
| Benzyl - 70 | 0 | 0 | 100 |
| Benzyl - 35 | 0 | 3 | 81 |
| Benzyl - 17.5 | 0 | 0 | 43 |

TABLE 17-continued

In-Water Applied Activity of Compound A

| | Mean Visual Injury (%) - 21 DAA | | |
|---|---|---|---|
| Compound A* g ae/ha | ORYSA - 'M202' | ORYSA - 'Wells' | ECHCG |
| Benzyl - 8.75 | 0 | 0 | 23 |
| 0 | 0 | 0 | 0 |

The present invention is not limited in scope by the embodiments disclosed herein which are intended as illustrations of a few aspects of the invention and any embodiments which are functionally equivalent are within the scope of this invention. Various modifications of the compositions and methods in addition to those shown and described herein will become apparent to those skilled in the art and are intended to fall within the scope of the appended claims. Further, while only certain representative combinations of the composition components and method steps disclosed herein are specifically discussed in the embodiments above, other combinations of the composition components and method steps will become apparent to those skilled in the art and also are intended to fall within the scope of the appended claims. Thus a combination of components or method steps may be explicitly mentioned herein; however, other combinations of components and method steps are included, even though not explicitly stated. The term comprising and variations thereof as used herein is used synonymously with the term including and variations thereof and are open, non-limiting terms.

What is claimed is:

1. A safened herbicidal composition for use in rice comprising a herbicidally effective amount of (a) benzyl ester of a compound of the formula (I)

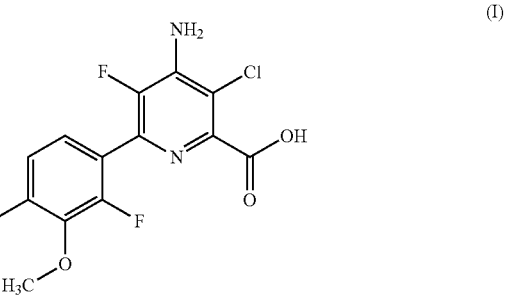

or an agriculturally acceptable salt or ester thereof and (b) a safener or a compatible herbicide capable of safening, wherein the compatible herbicide capable of safening is bispyribac-sodium, carfentrazone-ethyl, cyhalofop-butyl, diamuron, dimepiperate, halosulfuron-methyl, norflurazon, pyriclor, or sulcotrione.

2. The composition of claim 1, wherein (b) is a chemical from the quinolinyloxyacetate family of chemicals, dicyclonon, dichlormid, fenclorim, furilazole, isoxadifen-ethyl, mefenpyr-diethyl, naphthalic anhydride (NA), or agriculturally acceptable salts, esters, or mixtures thereof.

3. The composition of claim 2, wherein the chemical from the quinolinyloxyacetate family of chemicals is cloquintocet acid, cloquintocet mexyl, cloquintocet triisopropylamine, or cloquintocet dimethylamine.

4. The composition of claim 2, wherein the chemical from the quinolinyloxyacetate family of chemicals is cloquintocet mexyl.

5. The composition of claim 1, wherein the weight ratio of (a) to (b) is from 2:1 to 1:32.

6. The composition of claim 1, wherein the weight ratio of (a) to (b) is from 1:1 to 1:4.

7. The composition of claim 1, further comprising an agriculturally acceptable adjuvant or carrier.

8. The composition of claim 1, wherein the rice is direct-seeded, water-seeded, or transplanted paddy.

9. The composition of claim 1, wherein the rice is a glyphosate, glufosinate, dicamba, phenoxy auxin, pyridyloxy auxin, aryloxyphenoxypropionate, acetyl CoA carboxylase (ACCase) inhibitor, imidazolinone, acetolactate synthase (ALS) inhibitor, 4-hydroxyphenyl-pyruvate dioxygenase (HPPD) inhibitor, protoporphyrinogen oxidase (PPO) inhibitor, triazine, or bromoxynil tolerant rice possessing multiple or stacked traits conferring tolerance to multiple chemistries and/or multiple modes of action.

10. A method of controlling undesirable vegetation in rice comprising contacting the vegetation or applying to the soil or water adjacent thereto with a safened herbicidal composition comprising a herbicidally effective amount of (a) benzyl ester of a compound of the formula (I)

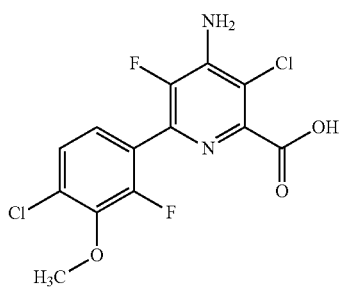

(I)

or an agriculturally acceptable salt or ester thereof and (b) a safener or a compatible herbicide capable of safening, wherein the compatible herbicide capable of safening is bispyribac-sodium, carfentrazone-ethyl, cyhalofop-butyl, diamuron, dimepiperate, halosulfuron-methyl, norflurazon, pyriclor, or sulcotrione.

11. The method of claim 10, wherein (b) is a chemical from the quinolinyloxyacetate family of chemicals, dicyclonon, dichlormid, fenclorim, furilazole, isoxadifen-ethyl, mefenpyr-diethyl, naphthalic anhydride (NA), or agriculturally acceptable salts, esters, or mixtures thereof.

12. The method of claim 11, wherein the chemical from the quinolinyloxyacetate family of chemicals is cloquintocet acid, cloquintocet mexyl, cloquintocet triisopropylamine, or cloquintocet dimethylamine.

13. The method of claim 11, wherein the chemical from the quinolinyloxyacetate family of chemicals is cloquintocet mexyl.

14. The method of claim 10, wherein the weight ratio of (a) to (b) is from 2:1 to 1:32.

15. The method of claim 10, wherein the weight ratio of (a) to (b) is from 1:1 to 1:4.

16. The method of claim 10, further comprising an agriculturally acceptable adjuvant or carrier.

17. The method of claim 10, wherein the rice is direct-seeded, water-seeded, or transplanted rice.

18. The method of claim 10, wherein the undesirable vegetation is immature.

19. The method of claim 10, wherein the (a) and (b) are applied to water.

20. The method of claim 19, wherein the water is part of a flooded rice paddy.

21. The method of claim 10, wherein the (a) and (b) are applied pre-emergently to the weed or the crop.

22. The method of claim 10, wherein the (a) and (b) are applied post-emergently to the weed or the crop.

23. The method of claim 10, wherein the rice is glyphosate, glufosinate, dicamba, phenoxy auxin, pyridyloxy auxin, aryloxyphenoxypropionate, acetyl CoA carboxylase (ACCase) inhibitor, imidazolinone, acetolactate synthase (ALS) inhibitor, 4-hydroxyphenyl-pyruvate dioxygenase (HPPD) inhibitor, protoporphyrinogen oxidase (PPO) inhibitor, triazine, or bromoxynil tolerant.

24. The method of claim 23, wherein the rice possesses multiple or stacked traits conferring tolerance to multiple chemistries and/or multiple modes of action.

* * * * *